United States Patent [19]

Ludtka et al.

[11] Patent Number: 5,750,882
[45] Date of Patent: May 12, 1998

[54] GAS PERMEABILITY MEASUREMENTS FOR FILM ENVELOPE MATERIALS

[75] Inventors: Gerard M. Ludtka; Thomas G. Kollie, both of Oak Ridge; David C. Watkin, Clinton; David G. Walton, Knoxville, all of Tenn.

[73] Assignee: Lockheed Martin Energy Research Corporation, Oak Ridge, Tenn.

[21] Appl. No.: 832,824

[22] Filed: Apr. 4, 1997

[51] Int. Cl.[6] .................................................. G01N 15/08
[52] U.S. Cl. .................................................. 73/38; 428/69
[58] Field of Search .................................. 73/38; 428/69

[56] References Cited

U.S. PATENT DOCUMENTS

| | | |
|---|---|---|
| 4,213,327 | 7/1980 | Prescott et al. ........................... 73/38 |
| 4,668,551 | 5/1987 | Kawasaki et al. ........................ 428/69 |
| 5,157,960 | 10/1992 | Brehm et al. ............................. 73/38 |
| 5,513,515 | 5/1996 | Mayer ....................................... 73/38 |
| 5,591,898 | 1/1997 | Mayer ....................................... 73/38 |

Primary Examiner—Hezron E. Williams
Assistant Examiner—Jay L. Politzer
Attorney, Agent, or Firm—J. Kenneth Davis

[57] ABSTRACT

Method and apparatus for measuring the permeability of polymer film materials such as used in super-insulation powder-filled evacuated panels (PEPs) reduce the time required for testing from several years to weeks or months. The method involves substitution of a solid non-outgassing body having a free volume of between 0% and 25% of its total volume for the usual powder in the PEP to control the free volume of the "body-filled panel". Pressure versus time data for the test piece permit extrapolation to obtain long term performance of the candidate materials.

16 Claims, 4 Drawing Sheets

GAS PERMEABILITY MEASUREMENTS FOR FILM ENVELOPE MATERIALS

The United States Government has rights in this invention pursuant to contract no. DE-AC05-84OR21400 between the U. S. Department of Energy and Lockheed Martin Energy Systems, Inc.

FIELD OF THE INVENTION

The present invention relates to methods and apparatus for measuring the permeability of a film by a gas, and more particularly to methods and apparatus for measuring the permeability of a polymer laminate film, a metallized polymer laminate film, a metal film, or a metal sheet which comprises an envelope for a powder-filled evacuated insulation panel.

BACKGROUND OF THE INVENTION

The successful implementation of a super-insulating, powder-filled evacuated panel (PEP) requires long term stability of the insulating capability of the PEP. These panels maintain their excellent thermal resistances as long as the internal pressure of the PEP is very low, on the order of 0.1 to 10 mm Hg pressure. The usual construction of a PEP requires an outer barrier material which contains the super insulating powder under these vacuum conditions. The outer material can be a polymer laminate film, a metallized polymer laminate film, metal film, or metal sheet. Because the usable size of a PEP, often about two feet by two feet, is limited by construction methods as well as the final application dimension, the polymer laminate materials, whether metallized or not, provide desirable barrier materials because they will not conduct heat around the perimeter or outer surface of a PEP to the degree that a very high conducting metal envelope would. In addition, relatively simple heat sealing equipment can be used to seal the polymer laminates in contrast to more complex seam welding techniques for metallic containments. However, the performance of the polymer laminate films is limited by the permeance (or permeability) of the film to typical gaseous environments of nitrogen, oxygen, carbon dioxide, and water vapor that will be experienced in actual use of the PEP. As these gases diffuse through the polymer laminate, the internal pressure of the PEP increases which inevitably results in eventual degradation of the super insulating capabilities of the PEP. Therefore, it is important to select the best candidate materials for the outer barrier material of the PEP as many laminate combinations can be made by the polymer industry. Unfortunately, the permeability of available films is generally not well characterized. Thus a potential manufacturer or user of PEP technology would be motivated to do some type of permeability study.

The powders inside a PEP typically are only at a fraction of a theoretical density (on the order of 7 to 15%) which means that there is a large free volume (about 90%) within the PEP. Defining equations for the pressure rise in a PEP show that the ratio of the surface area of the PEP envelope to the free internal volume must be maximized to observe the most rapid pressure rise in a PEP. Unfortunately, several years (about five years for 0.1 mm thick VECAT film laminate) would be required to observe an increase in internal pressure from 1 mm Hg to 5 mm Hg inside a conventional PEP. Permeability testing of this duration would be impractical, expensive, and equipment-intensive, especially when product lifetimes of 20 years are required for refrigerator/freezer PEPs and 100 years for home insulation PEPs. An inexpensive, rapid (less than six months) method of characterizing the permeance of different candidate materials is accomplished by this invention.

OBJECTS OF THE INVENTION

Accordingly, it is an object of the present invention to provide a new and improved method for measuring the permeability of a film by a gas, and more particularly for measuring the permeability of a polymer laminate film, a metallized polymer laminate film, a metal film, or a metal sheet which comprises an envelope for a powder-filled evacuated insulation panel.

It is another object to provide a new and improved apparatus for measuring the permeability of a film by a gas, and more particularly for measuring the permeability of a polymer laminate film, a metallized polymer laminate film, a metal film, or a metal sheet which comprises an envelope for a powder-filled evacuated insulation panel.

Further and other objects of the present invention will become apparent from the description contained herein.

SUMMARY OF THE INVENTION

In accordance with one aspect of the present invention, the foregoing and other objects are achieved by a method for determining the permeability of an envelope material of a given composition and thickness which comprises the steps of: providing an envelope comprising an envelope material, said envelope material having a material composition and a thickness, said envelope having an envelope volume; providing a body, said body having a total body volume and a free volume, the free volume being from 0% to about 25% of the total volume and being interconnected with the surface of said body, said body comprising a non-outgassing material, said body suitably sized and shaped to be contained within said envelope; sealing said body within said envelope while maintaining a partial vacuum within said envelope to provide a body-filled panel; disposing said body-filled panel within a sealable test enclosure; disposing a gas environment within said test enclosure, surrounding said body-filled panel, while maintaining a constant temperature and pressure within said gas environment for a specified period of time; measuring the pressure within said body-filled panel during the specified period of time; determining the relationship between pressure within said body-filled panel and elapsed time during the exposure of said body-filled panel to said gas environment; and calculating, from the relationship between said free volume of said body-filled panel, said pressure within said body-filled panel, and elapsed time during the exposure of said body-filled panel to said gas environment, the permeability of the envelope material to the gas.

In accordance with a second aspect of the present invention, the foregoing and other objects are achieved by: apparatus for determining the permeability of an envelope material of a given composition and thickness which comprises: an envelope comprising the envelope material, said envelope material having a thickness, said envelope having an envelope volume; a body, said body having a total body volume and a free volume, the free volume being from 0% to about 25% of the total volume and being interconnected with the surface of said body, said body comprising a non-outgassing material, said body suitably sized and shaped to be contained within said envelope; means for sealing said body within said envelope while maintaining a partial vacuum within said envelope to provide a body-filled panel; a test enclosure, said test enclosure being sealable to contain a gas environment therein, said gas environment having controllable temperature and pressure, said test enclosure further comprising means for disposing said body-filled panel within said test enclosure; means for disposing said gas environment within said test enclosure, surrounding said body-filled panel, while maintaining a constant temperature and pressure within said gas environment for a specified period of time; means for measuring the internal pressure within said body-filled panel during the specified period of time; means for determining the relationship between pressure within said body-filled panel and elapsed time during the exposure of said body-filled panel to said gas environment, and; means for calculating, from the relationship between said free volume of said body-filled panel, said pressure within said body-filled panel, and elapsed time during the exposure of said body-filled panel to said gas environment, the permeability of the envelope material to the gas.

For a better understanding of the present invention, together with other and further objects, advantages and capabilities thereof, reference is made to the following disclosure and appended claims in connection with the above-described drawings.

DETAILED DESCRIPTION OF THE INVENTION

Figure 1:
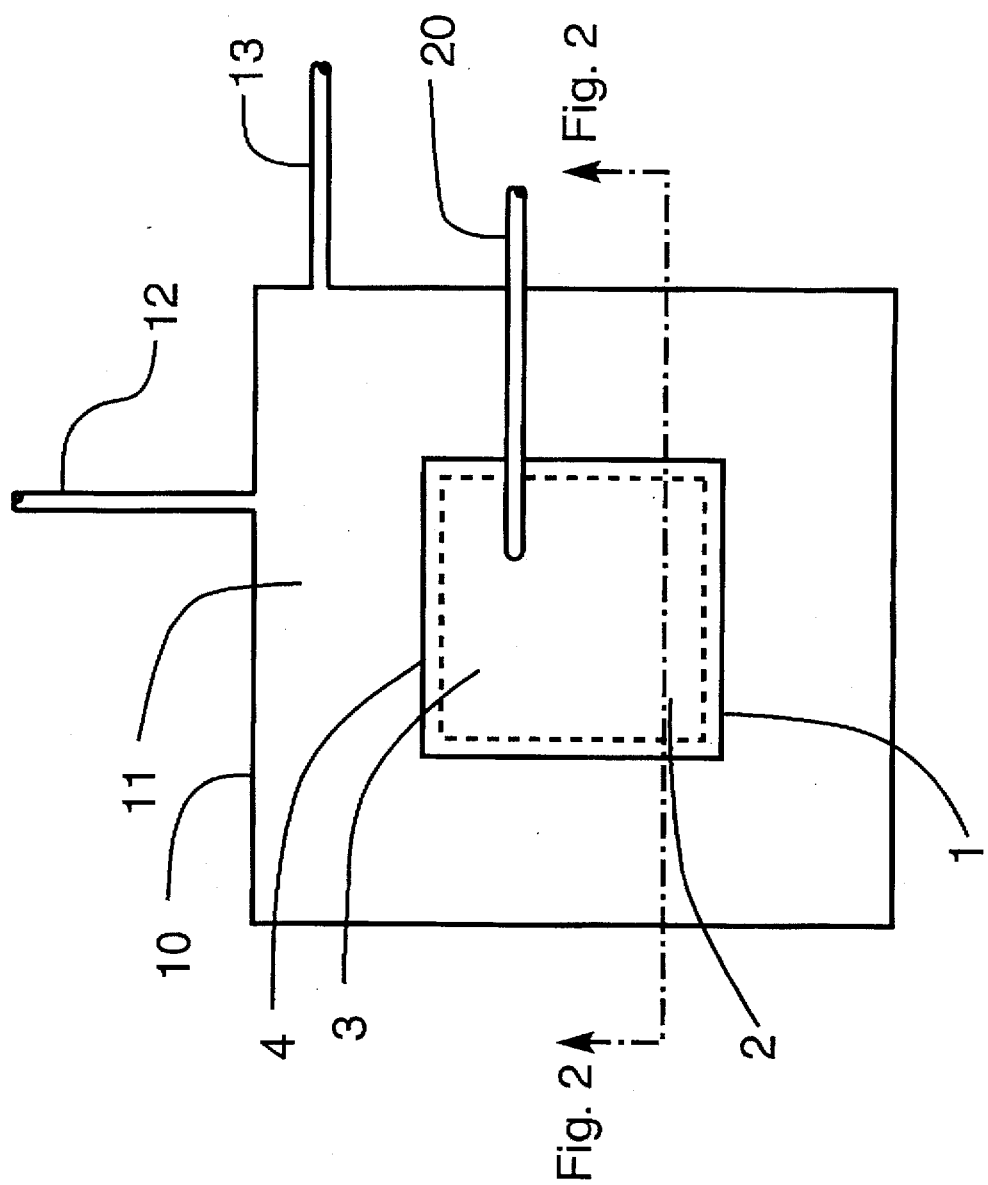
FIG. 1 is a schematic view of an apparatus for determining the permeability of an envelope material in accordance with the present invention, showing a body-filled panel contained within the test chamber.

A body-filled panel 1 comprises an envelope 2 and a body 3, as is shown in FIG. 1. The body is contained within the envelope by a vacuum-tight seal 4. The body-filled panel is contained within a test enclosure 10 which contains a gas environment 11 surrounding the body-filled panel 1. The gas environment is controlled by means for disposing the gas environment and controlling the gas pressure and temperature 12. Means for controlling the composition of the gas environment and the gas temperature 13 are provided. Also provided are means for measuring the internal gas pressure within the body-filled panel 20.

Figure 2:
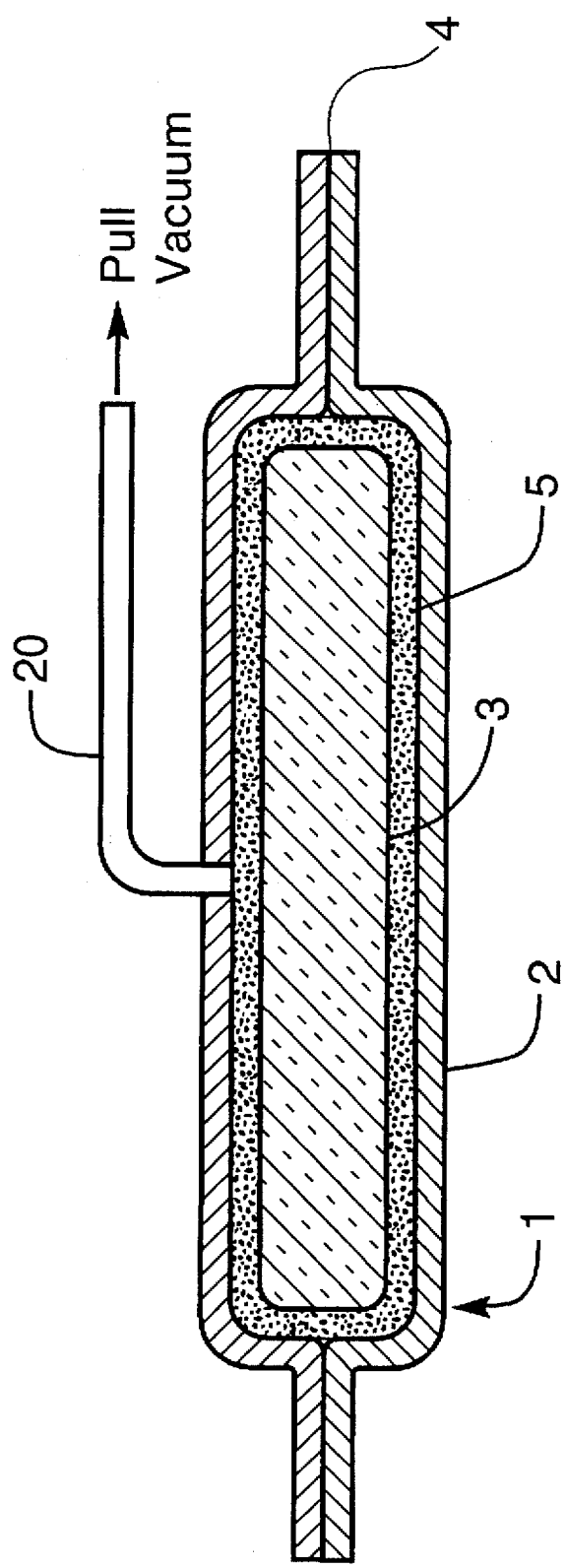
FIG. 2 is a cross-sectional view through A—A' of FIG. 1.

The body 3 is enclosed within an envelope 2 made vacuum-tight by seal 4, as is shown in cross-section in FIG. 2. An optional inner envelope 5 may be positioned between the envelope 2 and body 3. Means is for measuring the internal gas pressure within the body-filled panel 20 are provided. The body 3 is a porous or solid, non-outgassing body, or a solid, non-porous, non-outgassing body with precision machined holes to establish a very specific initial free volume value is placed within the bag or envelope 2 constructed of the candidate barrier material under vacuum conditions. The inner bag or envelope 5 which is constructed of mesh or semi-porous, non-outgassing material may be utilized between the non-porous body and the barrier material to prevent the barrier material from sticking to the non-porous body, if desired.

An aluminum plate with and without precision machined holes has been used for a non-porous body and Tyvek® has been used between the non-outgassing body and the barrier material. A Hollymatic heat sealer, often used in the meat vacuum packaging industry has been used for sealing the barrier material. The evacuated barrier material envelope containing the non-outgassing body, hereinafter called the body-filled panel is removed from the sealing system and the internal pressure is measured and recorded using some technique such as the fiber optic/baritron (capacitance manometer), hand-held gage, or in the Radial Heat Flow Apparatus (bell jar type vacuum system).

The body-filled panel is placed in a sealed test chamber in which the gaseous environment (gas composition, gas pressure, and gas temperature) is controlled. It is desirable that the body-filled panel be placed within the test chamber in a manner which allows gas exposure on all surfaces of the panel. Placing the body-filled panel on an open mesh shelf was found to be satisfactory.

The test chamber is operated at a specified test temperature for the permeability study. The test chamber is closed and evacuated. Care is taken to keep the vacuum level at some finite amount (about 20 mm Hg pressure) above the internal pressure of the body-filled panel which generally is on the order of 0.1 to 10 mm Hg. The system is backfilled to ambient atmospheric pressure or slightly higher (generally not above 780 mm Hg total chamber pressure) with the gas to be used in the permeability study. Evacuating and backfilling is repeated several times to insure that residual, unwanted gas species, such as water vapor, are not present inside the test chamber. The demonstration experiments for this invention typically operated at 775 mm Hg and a temperature of 90° F. after three evacuation/backfill cycles. The chamber internal pressure was typically measured using capacitance manometer gages that were set to 0.00 mm Hg at nominally 0.01 mm Hg using a Hastings gage adjacent to the manometer. Temperatures of the chambers were monitored using three thermocouples that were mounted to the exterior of the chambers; one on the door, one on the outer chamber surface, and one on the back surface of the chamber. The specimens were left in the chambers for varying amounts of time which were dependent on the gas environment and its suspected permeation rate through the barrier materials. Typically, the chambers were opened and the body-filled panel internal pressures measured at two-week time intervals when exposure was in dry nitrogen or dry air. Only one to two days would be allowed to elapse between measurements if the environment were dry helium since helium permeates on the order of approximately a thousand times faster in polymeric film laminate barrier materials than nitrogen or oxygen. Care must be taken to ensure that all of the internal pressure measurements are performed on the body-filled panels at the same nominal temperature (within each sampling period and between each sampling period) since different sample temperatures would change the volume of the internal gas and therefore the pressure read could vary as well as the panel would change volume due to thermal expansion/contraction and affect the reading critical for the permeation study.

Figure 3:
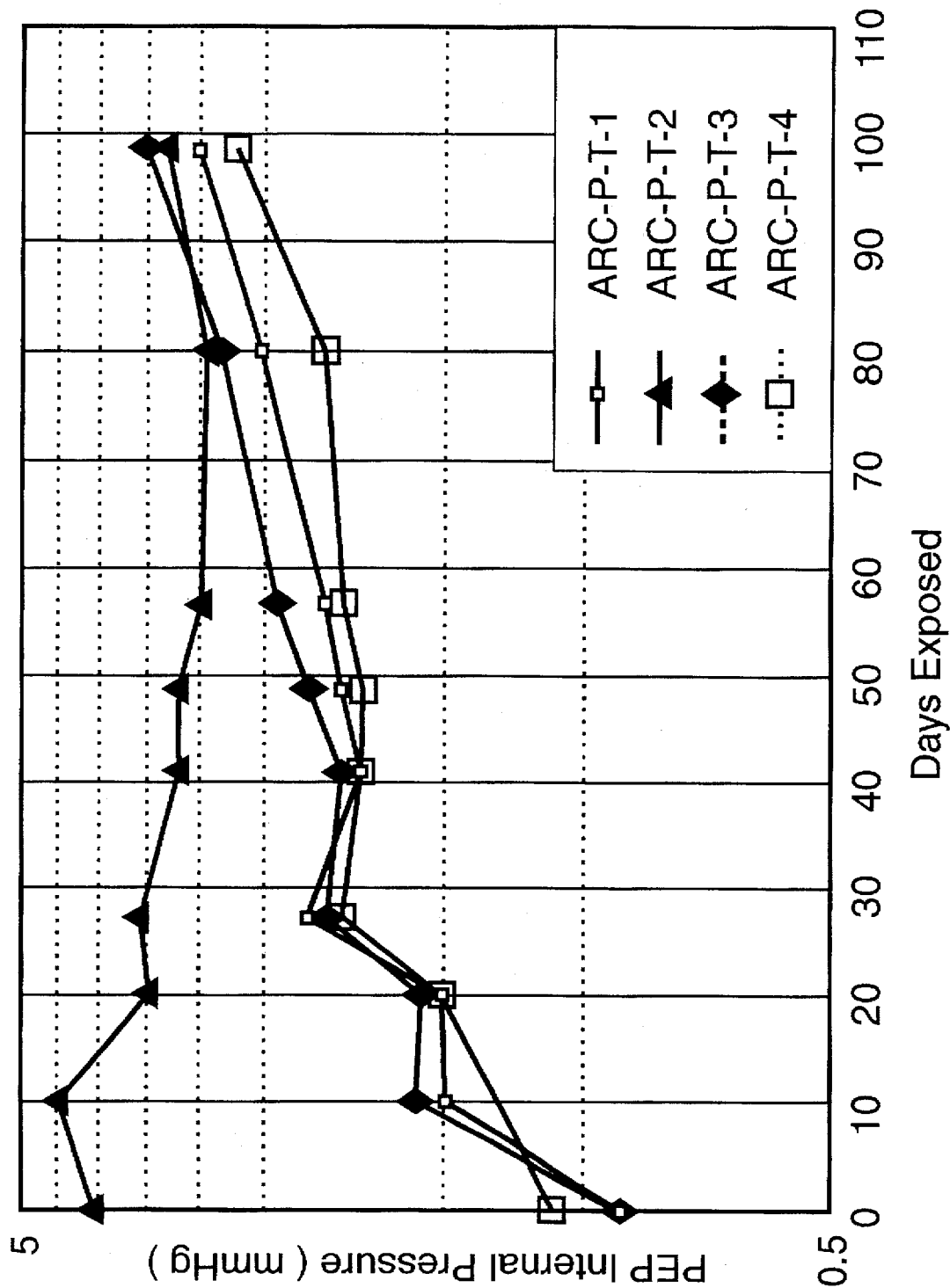
FIG. 3 shows log pressure versus time for the pressure in the free volume within a typical body-filled panel for a permeation rate study in dry nitrogen at 90° F. (32.2° C.). A solid aluminum body is encapsulated in VECAT over a layer TYVEK®.
Figure 4:
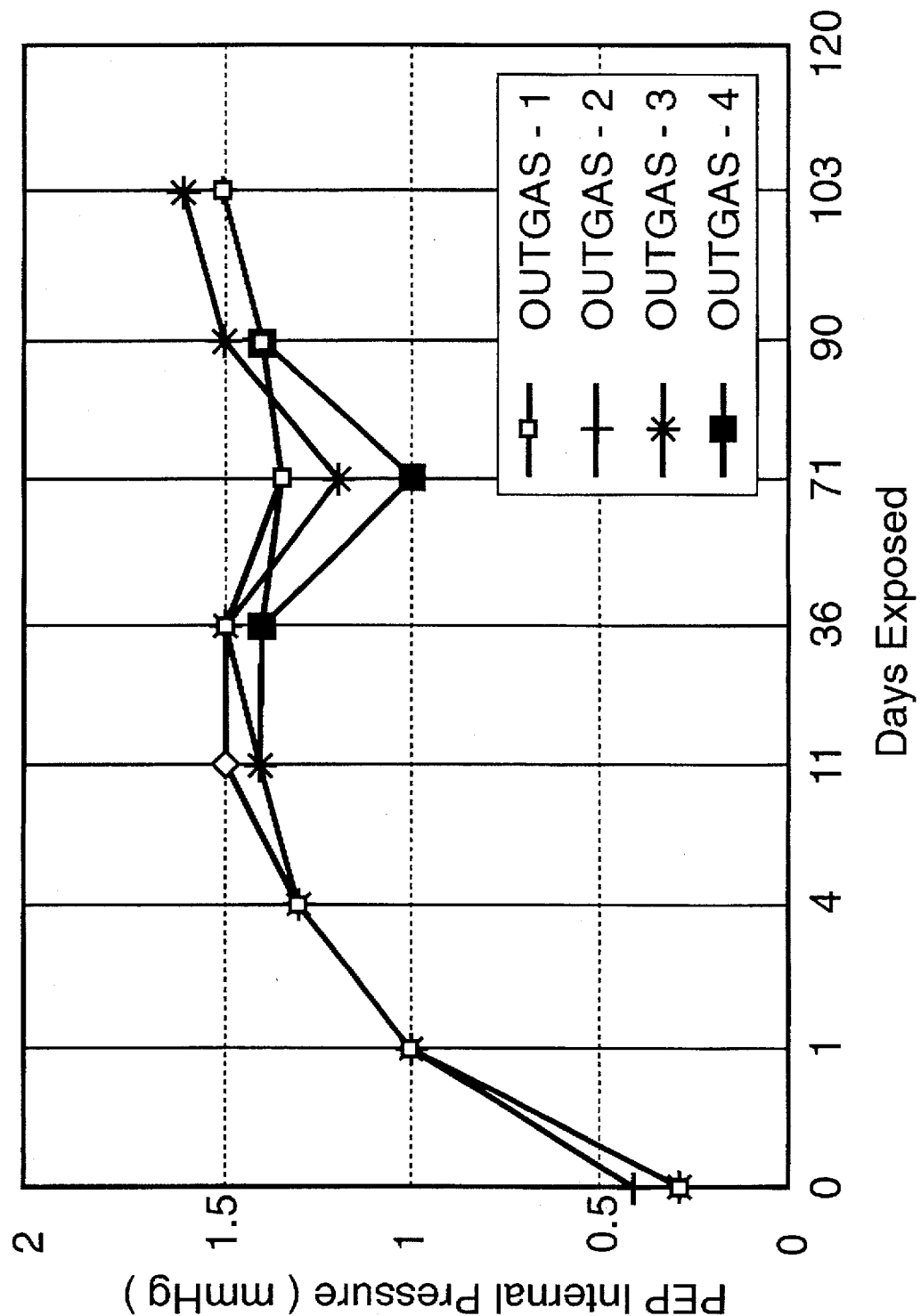
FIG. 4 shows log pressure versus time for the pressure in the free volume within a typical powder-filled panel for a powder outgassing study in dry air at 90° F. (32.2° C.). The powder is T600 (prebaked overnight at 120° C.). The powder is enclosed in a TYVEK® powder bag and encapsulated in VECAT 0.1 mm thick.

An example of the body-filled panel internal pressure rise monitored with time for a 0.1 mm thick VECAT barrier material is shown in FIG. 3 for a dry nitrogen environment. This relationship is contrasted to the internal pressure rise measured in ceramic powder-filled evacuated panels using a PPG Industries T600 powder that is labeled as a "powder outgassing" study which was exposed to a dry air environment. FIGS. 3 and 4 respectively clearly show that the unique idea of using a minimized internal free volume panel such as the aluminum panel definitely accelerates the internal pressure rise measured over an extended time period whereas the pressure versus time history in the powder-filled evacuated panels using the same 0.1 mm thick VECAT barrier material show no real measurable pressure rise for the same time period after the initial pressure rise caused by powder outgassing at the very early stage of exposure. This outgassing is attributable to the very large surface area of the powders used in PEPs (typically 175 m$^2$/g) and is possibly from absorbed water, oxygen, or nitrogen. The lack of any significant internal pressure rise is directly attributable to the very large internal free volume of this type of PEP. The powders typically are at very low theoretical densities (7% to 20%) and the internal free volume for a 0.23 m×0.23 m×0.01 m ceramic powder filled PEP is on the order of 468 cm$^3$. This is in contrast to the minimized free volume (in reality, maximization of the PEP barrier material permeating surface area, A, divided by the internal free volume, V) solid aluminum body-filled panels which have an internal free volume on the order of about 0.4 cm$^3$. Using aluminum bodies with precision machined holes or using bodies constructed of a non-outgassing porous material with interconnecting pores allows a relatively precise finite free volume to be selected by the user. Typically a small value of free volume is chosen to allow maximum pressure rise in a reasonable time period. This latter approach is used when the initial free volume of the solid body-filled panel construction is uncertain. Not much gas has to permeate through the barrier material in the aluminum body-filled panel to cause a pressure rise in the very small free volume, whereas a significant amount of gas would have to permeate through the barrier material in the powder-filled evacuated panels to cause a pressure rise in the very large (468 cm$^3$) internal free volume of the powder.

Using literature data for the permeance of oxygen through VECAT and a powder-filled evacuated panel of the above dimensions, an exposure time of 10.6 years is calculated for the PEP internal pressure rise to occur from 0.3 mm Hg to 5.0 mm Hg. The accelerated rate, body-filled panel tests in dry nitrogen, which permeates at only approximately one-fourth the rate of oxygen, clearly show that a very significant internal pressure rise of 3.0 to 3.5 mm Hg occurs in a little over 100 days. This verifies the concept of an accelerated permeation rate procedure/system for barrier material permeation rate studies.

After sufficient exposure time (but significantly shorter time for the aluminum body-filled panel than would be required if a conventional powder-filled evacuated panel were used), which is dependent on the permeating gas species, a steady state condition develops which will yield a straight line slope on a log pressure versus time plot (see FIG. 3). This slope is relatable to the permeance of the gas, p, through the barrier material and the internal free volume, V, of the PEP as follows:

$$\text{SLOPE} = (-pATRd_o)/(VM)$$

where "p" is the gas permeance, "A" is the permeating surface area of the PEP barrier material, "T" is the test temperature, "R" is the ideal gas constant, "$d_o$" is the density of the gas at STP (Standard Temperature and Pressure), "V" is the PEP internal free volume, and "M" is the molecular weight of the permeating gas. Once the internal free volume of the PEP is known, the "steady state" permeance can be calculated from the linear slope since all of the other parameters are known.

The free volume of the body-filled panel can be determined using either of two methods. In the first method, a controlled leak rate source is attached to a sacrificial body-filled panel through a barrier material feedthrough device. The sample is evacuated to the initial vacuum level that a normal body-filledpanel would be fabricated under. The internal pressure is measured using equipment described earlier and recorded. The controlled leak rate source is then activated for a specified amount of time which allows a known volume (and moles, $\Delta n$) of gas, $\Delta V$, to fill the inside of the sacrificial panel. The internal pressure is again measured and recorded. From the ideal gas law: (PV=nRT) two equations can be written in terms of $P_1$, $P_2$, $V_1$, $\Delta V$, $n_1$, $\Delta n_1$, and $T_1$. Since there are only two unknowns, specifically $n_1$ and $V_1$, this system of equations can easily be solved for the initial internal free volume, $V_1$, of the body-filled panel for this barrier material. The internal volume of the feedthrough device must be known and accounted for (subtracted out afterwards) in these calculations.

The second method for determining the approximate free volume of the body-filled panel involves encapsulating the body with a barrier material whose permeance in a specific environment is well known and documented, e.g., a traceable NIST-type standard material. The body-filled panel is treated as a normal permeation study sample and exposed to the specific gaseous environment until a straight line slope is obtained for the log pressure versus exposure time plot. The slope is directly relatable to all known quantities with the exception of the internal free volume, V, which can easily be calculated from the slope and known property data.

After one gas environment has been studied, the samples can be moved to another chamber or the same chamber can be used with a new gas environment such as dry air or helium. Similar procedures are employed as described above for the nitrogen exposure and the value of the permeance for oxygen can be back-calculated from the dry air data using the value of the nitrogen permeance from the initial study. A pure oxygen chamber could be used, but use of pure oxygen is more dangerous. If helium were the environment of interest, the gas permeance through the barrier material could be calculated similarly with the exception that significantly shorter exposure times would be required to obtain this information.

Use of an aluminum panel with precision machined holes allows an alternative approach to initial free volume determination. The free volume of these aluminum panels with holes does not have to be experimentally determined. This free volume will essentially be the sum of all of the free volumes of the individual holes. Likewise, use of a porous material with interconnecting pores provides a known free volume. The ratio of the density of the porous material to the density of the material without pores can be used to calculate the free volume by methods well known to the skilled artisan. The value of free volume should be chosen such that neglecting contributions of wrinkles in the barrier material (VECAT) and the open volume in the inner bag (Tyvek®) membrane to the total free volume is justifiable (negligible) within the experimental error of obtaining these very small quantities.

The long term life of the barrier material for use in PEPs could finally be evaluated by ratioing the helium/nitrogen, helium/air (oxygen) or air (oxygen)/nitrogen permeances. In this manner, internal pressure rises for conventional, super-insulation powder-filled evacuated panels under ambient gaseous environments may be predicted for exposure times of 20 years for refrigerator/freezer applications and 100 years for home insulation use.

While there has been shown and described what are at present considered the preferred embodiments of the invention, it will be obvious to those skilled in the art that various changes and modifications can be made therein without departing from the scope of the inventions defined by the appended claims.

We claim:

1. A method for determining the permeability of an envelope material of a given composition and thickness comprising the steps of:

a providing an envelope comprising an envelope material, said envelope material having a material composition and a thickness, said envelope having an envelope volume;

b providing a body, said body having a total body volume and further having means for establishing a specific initial free volume, said means for establishing a specific initial free volume selected from at least one of the group of means consisting of pores and precision-machined holes, the free volume being from 0% to about 25% of the total volume and being interconnected with the surface of said body, said body comprising a solid, non-outgassing material, said body suitably sized and shaped to be contained within said envelope;

c sealing said body within said envelope while maintaining a partial vacuum within said envelope to provide a body-filled panel;

d disposing said body-filled panel within a sealable test enclosure;

e disposing a gas environment within said test enclosure, surrounding said body-filled panel, while maintaining a constant temperature and pressure within said gas environment for a specified period of time;

f measuring the pressure within said body-filled panel during the specified period of time;

g determining the relationship between pressure within said body-filled panel and elapsed time during the exposure of said body-filled panel to said gas environment; and h calculating, from the relationship between said free volume of said body-filled panel, said pressure within said body-filled panel, and elapsed time during the exposure of said body-filled panel to said gas environment, the permeability of the envelope material to the gas.

2. The method as described in claim 1 wherein said envelope material comprises a material selected from the group consisting of polymer laminate films, metallized polymer laminate films, metal films, and metal sheets.

3. The method as described in claim 1 wherein said body material comprises a metal.

4. The method as described in claim 1 wherein said gas environment comprises gases selected from the group of gases consisting of helium, nitrogen, oxygen, air, and mixtures thereof.

5. The method as described in claim 1 wherein said internal pressure of the partial vacuum within the envelope when it is sealed is about 0.1 to 10 mm Hg.

6. The method as described in claim 1 further comprising the steps of providing an inner envelope comprising an inner envelope material and placing said inner envelope between said body and said envelope, said inner envelope separating said body from said envelope.

7. The method as described in claim 6 wherein said envelope material comprises a material selected from the group consisting of open mesh materials, porous materials, and semi-porous materials.

8. The method as described in claim 7 wherein said inner envelope material is Tyvek®.

9. Apparatus for determining the permeability of an envelope material of a given composition and thickness comprising:

a an envelope comprising the envelope material, said envelope material having a thickness, said envelope having an envelope volume;

b a body, said body having a total body volume and further having means for establishing a specific initial free volume, said means for establishing a specific initial free volume selected from at least one of the group of means consisting of pores and precision-machined holes, the free volume being from 0% to about 25% of the total volume and being interconnected with the surface of said body, said body comprising a solid, non-outgassing material, said body suitably sized and shaped to be contained within said envelope;

c means for sealing said body within said envelope while maintaining a partial vacuum within said envelope to provide a body-filled panel;

d a test enclosure, said test enclosure being sealable to contain a gas environment therein, said gas environment having controllable temperature and pressure, said test enclosure further comprising means for disposing said body-filled panel within said test enclosure;

e means for disposing said gas environment within said test enclosure, surrounding said body-filled panel, while maintaining a constant temperature and pressure within said gas environment for a specified period of time;

f means for measuring the internal pressure within said body-filled panel during the specified period of time;

g means for determining the relationship between pressure within said body-filled panel and elapsed time during the exposure of said body-filled panel to said gas environment, and;

h means for calculating, from the relationship between said free volume of said body-filled panel, said pressure within said body-filled panel, and elapsed time during the exposure of said body-filled panel to said gas environment, the permeability of the envelope material to the gas.

10. The apparatus as described in claim 9 wherein said envelope material comprises a material selected from the group consisting of polymer laminate films, metallized polymer laminate films, metal films, and metal sheets.

11. The apparatus as described in claim 9 wherein said body material comprises a metal.

12. The apparatus as described in claim 9 wherein said gas environment comprises gases selected from the group of gases consisting of helium, nitrogen, oxygen, air, and mixtures thereof.

13. The method as described in claim 9 wherein said internal pressure of the partial vacuum within the envelope when it is sealed is about 0.1 to 10 mm Hg.

14. The apparatus as described in claim 9 further comprising an inner envelope comprising an inner envelope material, the inner envelope being disposed between said body and said envelope, said inner envelope separating said body from said envelope.

15. The apparatus as described in claim 14 wherein said inner envelope material comprises a material selected from the group consisting of open mesh materials, porous materials, and semi-porous materials.

16. The apparatus as described in claim 14 wherein said inner envelope material comprises Tyvek®.

* * * * *